United States Patent
Wilson et al.

(10) Patent No.: US 6,312,430 B1
(45) Date of Patent: *Nov. 6, 2001

(54) BIPOLAR ELECTROSURGICAL END EFFECTORS

(75) Inventors: Jeffrey A. Wilson, Mendon, MA (US); John K. Danks, Delray Beach; Jim Young, Davie, both of FL (US)

(73) Assignee: Endoscopic Concepts, Inc., Delray Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/399,137

(22) Filed: Sep. 20, 1999

Related U.S. Application Data

(63) Continuation-in-part of application No. 08/942,133, filed on Oct. 1, 1997, now Pat. No. 5,954,720
(60) Provisional application No. 60/029,405, filed on Oct. 28, 1996.

(51) Int. Cl.[7] .................................................. A61B 18/14
(52) U.S. Cl. ............................... 606/50; 606/46; 606/48; 606/51; 606/170; 606/174
(58) Field of Search ........................... 606/45, 46, 48.52, 606/170, 174

(56) References Cited

U.S. PATENT DOCUMENTS

| | | | |
|---|---|---|---|
| 5,573,534 | * | 11/1996 | Stone ..................................... 606/48 |
| 5,860,975 | * | 1/1999 | Goble et al. ........................... 606/45 |
| 5,954,720 | * | 9/1999 | Wilson et al. ......................... 606/50 |
| 6,090,108 | * | 7/2000 | McBrayer et al. ..................... 606/46 |

FOREIGN PATENT DOCUMENTS

2680314 * 2/1993 (FR) ...................................... 606/51

* cited by examiner

*Primary Examiner*—Lee Cohen
(74) *Attorney, Agent, or Firm*—Douglas T. Johnson; Miller & Martin LLP

(57) ABSTRACT

A novel, bipolar, electrosurgical instrument is provided with two end effectors. Current is passed through the second end effector and through an insulated conduit to the distal tip of the first end effector. The first and second end effectors allow the current to travel along exposed conductive strips which are spaced apart cutting surfaces by a gap of preferably approximately 0.020–0.040 inches when the first and second blade supports are brought into contact with tissue. Current flows between the exposed metal strip on the first blade and the exposed metal strip on the second blade thereby effecting cauterization, preferably slightly in advance or at the point of cutting between the ceramic and metal blades. The first and second end effectors may be partially insulated to direct current between the conductive strips, and both may have gaps at their respective surfaces.

20 Claims, 8 Drawing Sheets

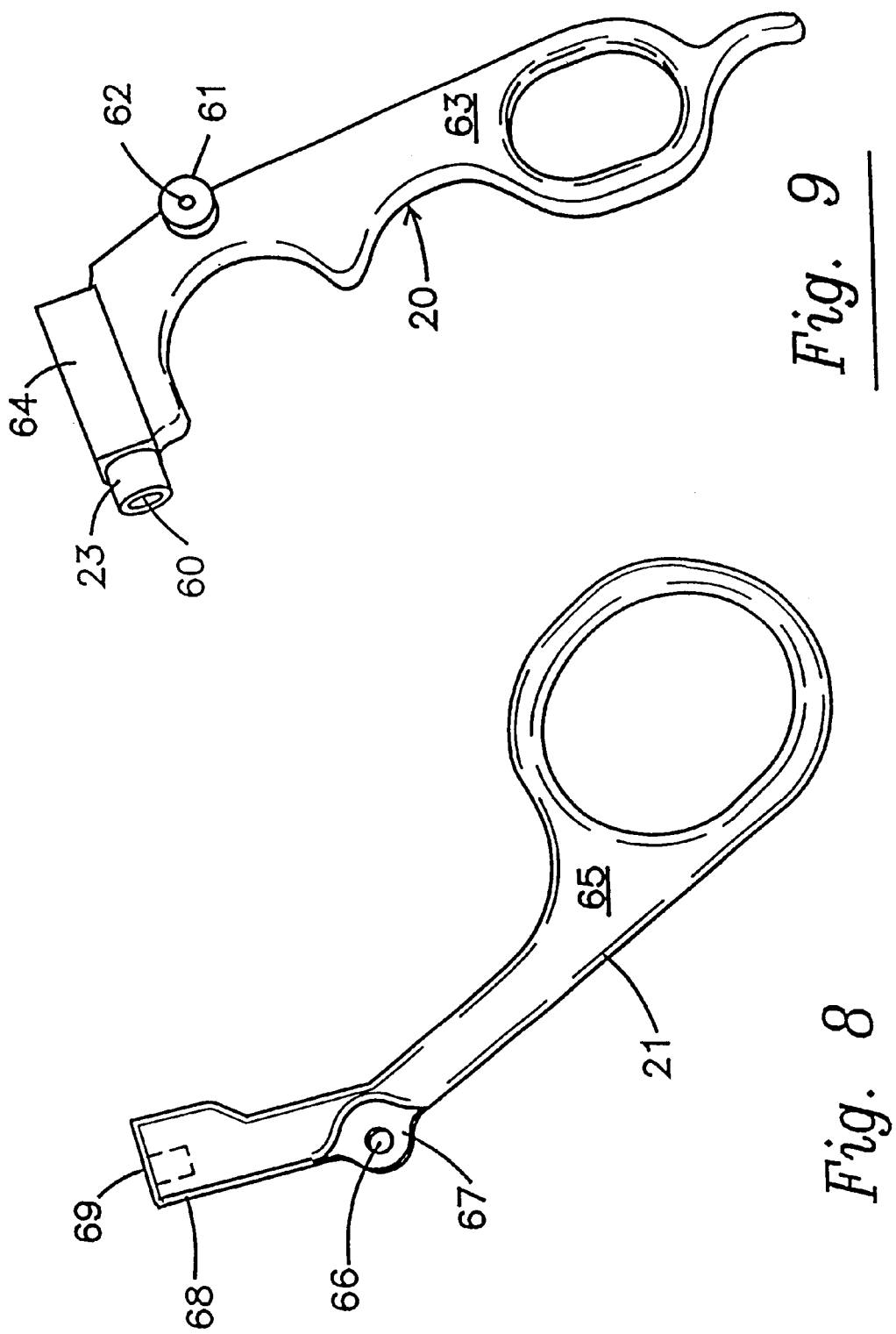

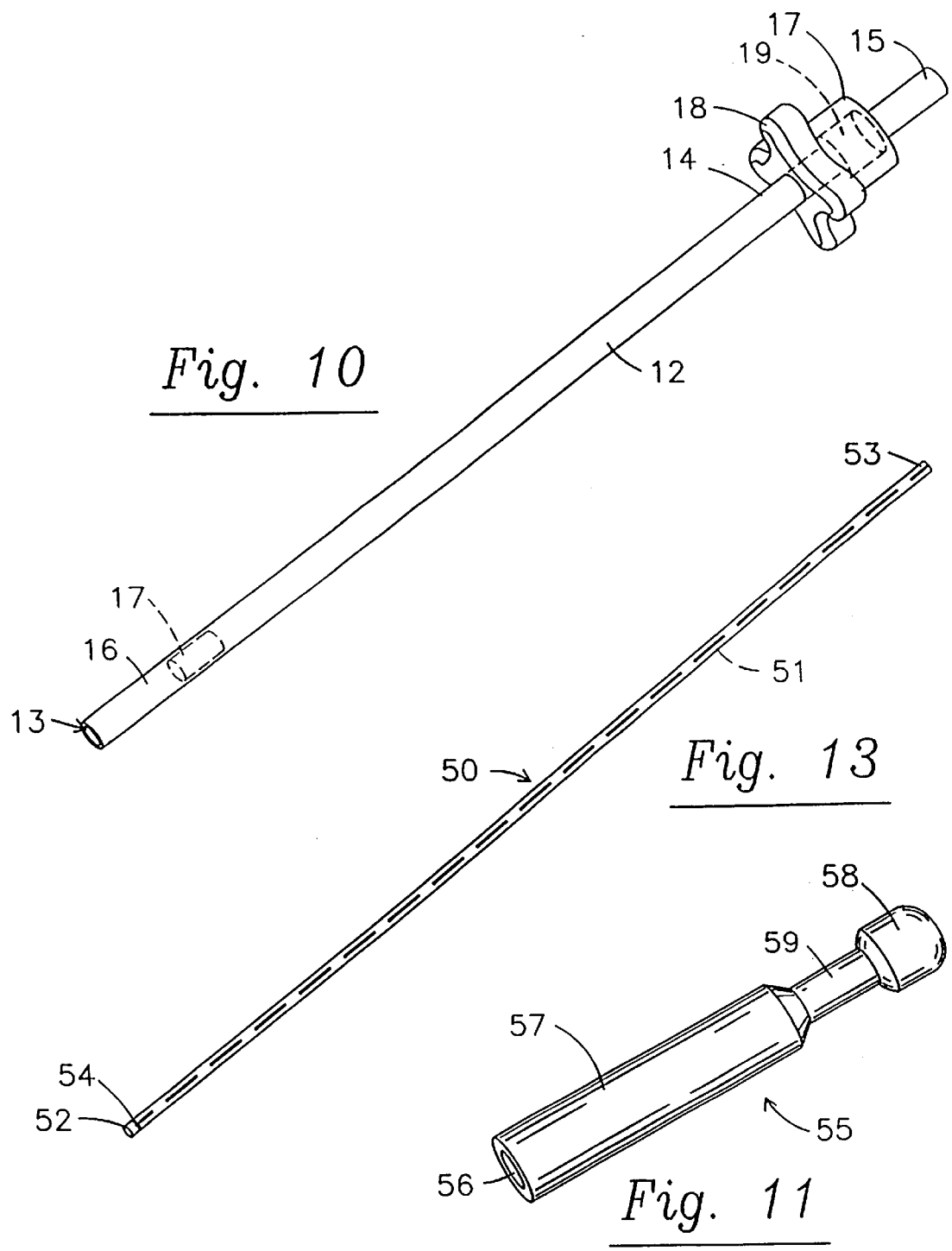

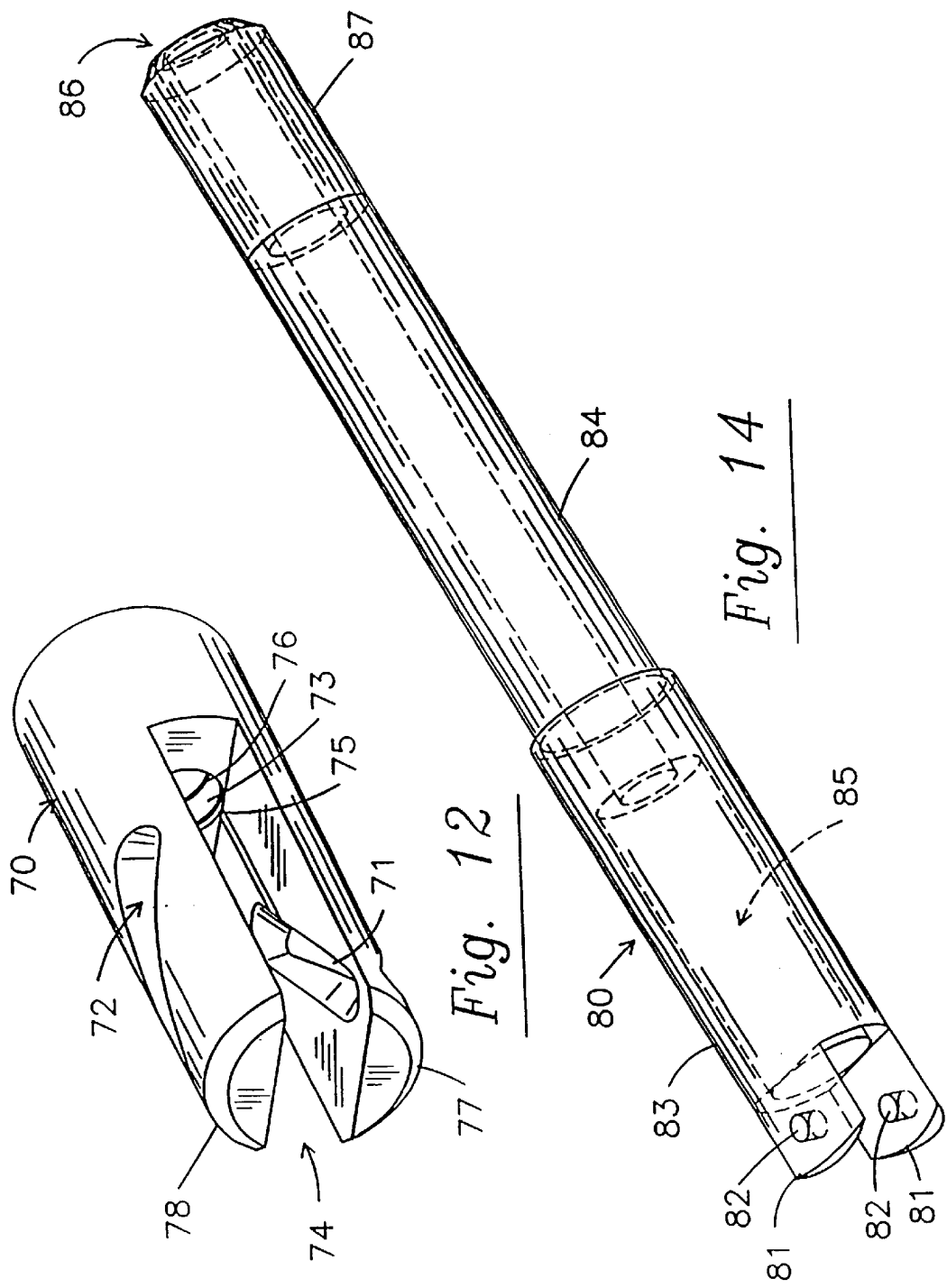

BIPOLAR ELECTROSURGICAL END EFFECTORS

This application is a continuation-in-part of U.S. patent application Ser. No. 08/942,133 filed Oct. 1, 1997, now U.S. Pat. No. 5,954,720 which claims the benefit of U.S. provisional application No. 60/029,405 filed Oct. 28, 1996.

BACKGROUND OF THE INVENTION

The present invention relates to endoscopic surgical instruments, and more particularly to instruments known as end effectors which may include cutters or scissors, graspers and dissectors which are useful in laparoscopic or endoscopic procedures. The surgical instruments made according to the present invention are bipolar to permit safe and effective dissection, incising and cauterization of blood vessels, bleeding tissues, or non-bleeding tissues.

The use of heat for the cauterization of bleeding wounds dates back for centuries. More recently, the use of radio frequency (RF) electrical current traveling through a portion of the body has been widely used to stop bleeding. The RF energy cauterizes the blood by heating the blood proteins to a temperature where those proteins congeal similarly to the process involved in the cooking of egg whites. RF energy is preferred because its frequency is above that which could otherwise cause neuromuscular stimulation. The most frequently used modes of RF cauterization are monopolar and bipolar coagulation.

In monopolar coagulation, an active electrode is applied to a bleeding site and the electrical current flows from the electrode through the patient's body to a return electrode which may be a conductive plate in electrical contact with a large surface area of the patient's body such as the buttocks or thigh. One technique in which the monopolar mode may be employed involves fulguration which is the use of a spark or arc from the active electrode to the tissue.

Bipolar devices include both the active and return electrodes. Thus the electrical current flows down the surgical instrument to the active electrode and typically crosses a space on the order of millimeters, or shorter, to the return electrode and returns through the surgical device. Because no external return electrode is required, bipolar electrical surgical devices have the inherent advantage of containing the RF energy in a defined area. This prevents potential patient complications related to monopolar RF energy traveling through the patient's body, such as the burning of nearby tissue or affecting the neurological function. The reduction of patient complications is also accomplished because bipolar devices typically require less RF energy than equivalent monopolar devices.

Endoscopic surgical instruments, such as the bipolar electrosurgical end effectors are often used in laparoscopic surgery, which is most commonly employed for cholecystectomies (gall bladder surgeries), hysterectomies, appendectomies, and hernia repair. These surgeries are generally initiated with the introduction of a Veress needle into the patient's abdominal cavity. The Veress needle has a stylet which permits the introduction of gas into the abdominal cavity. After the Veress needle is properly inserted, it is connected to a gas source and the abdominal cavity is insufflated to an approximate abdominal pressure of 15 mm Hg. By insufflating the abdominal cavity, a pneumoperitoneum is created separating the wall of the body cavity from the internal organs. A surgical trocar is then used to puncture the body cavity. The piercing tip or obturator of the trocar is inserted through the cannula or sheath and the cannula partially enters the body cavity through the incision made by the trocar. The obturator can then be removed from the cannula and an elongated endoscope or camera may be inserted through the cannula to view the body cavity, or surgical instruments such as bipolar electrosurgical end effectors according to the present invention, may be inserted to perform the desired procedure.

Frequently an operation using trocars will require three or four punctures so that separate cannula are available for the variety of surgical instruments which may be required to complete a particular procedure. As described in U.S. Pat. No. 5,258,006 for bipolar electrosurgical forceps, the alternatives to bipolar cauterization or coagulation have been unacceptable. Monopolar instruments, using RF energy, often require greater current and provide unpredictabilities in current flow which may have a destructive effect on tissues surrounding the area to be cauterized.

While non-contact positioning of a laser may overcome this shortcoming, the laser has no way of holding a bleeding vessel and is not used on large bleeders. Laser based cauterization instruments remain expensive and unsuitable for tissue dissection techniques other than cauterization, such as blunt dissection or sharp dissection. Laser cauterization instruments suffer from the additional shortcomings that it is difficult to control the depth of penetration of the laser energy and that non-contact positioning of a laser can permit the laser beam to reflect off of other instruments and cause damage to surrounding tissue.

Furthermore, as described in U.S. Pat. No. 5,472,443 for an electrosurgical apparatus, there have been difficulties in bipolar instruments in two primary areas. The first is the difficulty in preventing excessive trauma or charring to the tissue being cauterized. Such charring or tissue damage can impede healing and regrowth of tissue. In addition, bipolar instruments suffer from a buildup of coagulated blood or severed tissue. In prior art instruments, such buildup impeded the effectiveness of the cauterization action of the instrument, and also tended to cause recently cauterized tissue to adhere to the coagulated blood and tissue on the instrument resulting in tears and reopening of blood flows along the cut or incision. The invention described herein overcomes these shortcomings and may effectively reduce the number of surgical instruments required for a given procedure.

SUMMARY OF THE INVENTION

It is therefore an object of the invention to provide an improved surgical instrument with bipolar end effectors.

A further object of the invention is to provide an embodiment having two metal end effectors which are insulated except along portions for intended current travel.

Another object of the invention is to provide an embodiment having insulation on the back of at least one or both blades to prevent, or at least reduce current flow outside an intended current path.

It is a further object of at least one embodiment to pass current through the conducting strip of one end effector so that the coagulation caused by the RF energy tends to be very slightly in advance of or at the cutting point between the second and first end effectors, rather than rearward of the cutting point.

It is yet a further object of the invention to provide a bipolar instrument which utilizes RF energy more efficiently to cauterize tissue and thereby minimize charring of tissue.

Still, another object of the invention is to provide at least one notched blade which is believed to assist in providing tampon pressure at or near the intended severance path and assist in the defining of a more precise current travel path.

It is still a further object to provide an embodiment with two blades with corresponding notched portions which is believed to assist in providing tampon pressure and assist in the defining of a more precise current travel path.

Another object of the invention is to utilize electrodes in notched areas of the blades to focus the flow of current in the locale of the incision. This construction has been found to result in a greater current density in the incision by allowing RF current to flow directly through the incision instead of indirectly such that a stray current which may otherwise damage collateral tissue is significantly reduced.

These and other objects of the invention are accomplished by the utilization of one blade having a current conduit proceeding toward the distal end of the blade and therein connecting a conductive strip which proceeds rearward adjacent to the cutting surface of the blade. This blade is utilized to cut tissue in conjunction with a second blade. The second blade may, or may not, be similar in construction to the first blade, but the second blade will have a conducting strip capable of conducting current.

DESCRIPTION OF THE DRAWINGS

FIG. 8 is a side view of a moveable handle portion for a bipolar end effector.

FIG. 9 is a side view of a stationary handle portion for a bipolar end effector.

FIG. 10 is a perspective view of an elongated tubular barrel for end effectors having a grasping knob to facilitate rotation.

FIG. 11 is a perspective view of a push rod connector for use in an electrosurgical end effector.

FIG. 12 is a perspective view of a cam part according to the present invention.

FIG. 13 is a side view of an internal push rod adapted to transmit current or wire connectors through the tubular barrel of an electrosurgical end effector.

FIG. 14 is a perspective view of a clevis section used with bipolar end effectors made according to the present invention.

DESCRIPTION OF THE PREFERRED EMBODIMENT

Figure 1:
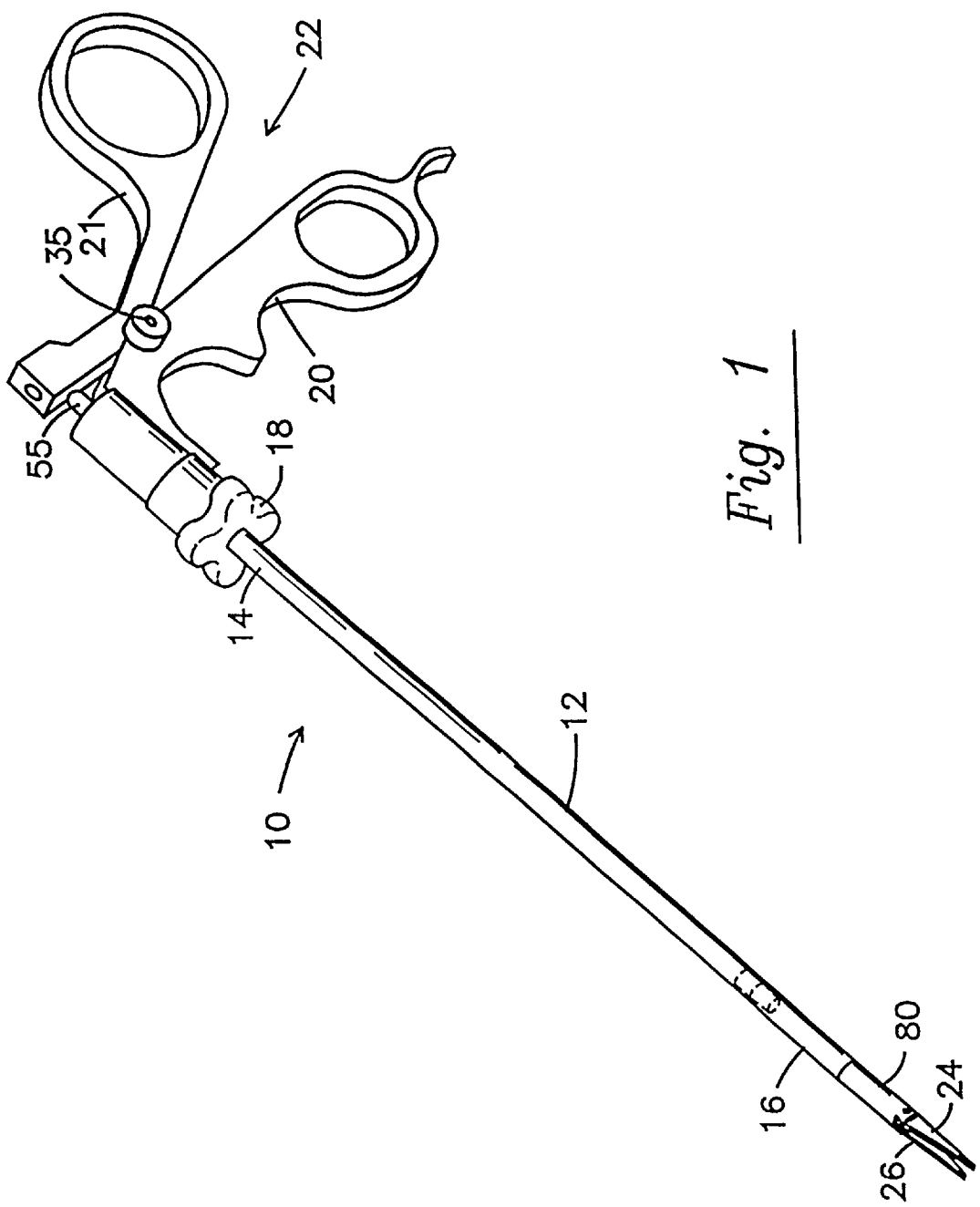
FIG. 1 is a perspective view of an endoscopic electrosurgical scissors constructed in accordance with the present invention.

Referring to FIG. 1, there is indicated generally by numeral 10 a bipolar electrosurgical scissors for endoscopic surgery constructed having end effectors in accordance with the present invention. It will be understood that the principles of the present invention are equally suitable for use in other bipolar end effector instruments such as graspers and dissectors.

Although many types of bipolar scissors are known in the art, this description will be directed at a single scissor type for ease of explanation. It should be obvious to one skilled in the art that any bipolar effector design, especially bipolar scissors, having end effectors as described herein are contemplated by this invention.

The scissors 10 are seen to typically include an elongated tubular barrel 12 having a proximal end 14 a distal end 16, and with a lumen extending there between. The outer diameter of the barrel 12 is sufficiently small to be passed through the working lumen of a trocar cannula. Tubular barrel 12 is preferably an insulated metal tube, as by Teflon coating, or a rigid plastic tube. Mounted on the proximal end 14 of the tubular barrel 12 of the bipolar scissors 10 is a knob 18 which facilitates rotation of the tubular barrel 12 and connected end effectors. The tubular barrel 12 and knob 18 are mounted to the stationary portion 20 of an actuator such as handle assembly 22.

Manipulation of moveable scissors handle 21 relative to stationary handle section 20 manipulates push rod connector 55 and push rod 50 (illustrated in FIG. 13) which is internal to push rod connector 55 and tubular barrel 12 and in linked communication with end effectors such as blades 24 and 26, which are thereby caused to move in scissors-like action relative to one another. Of course, other scissor designs may operate satisfactorily with the end effectors of the present design.

Figure 6A:
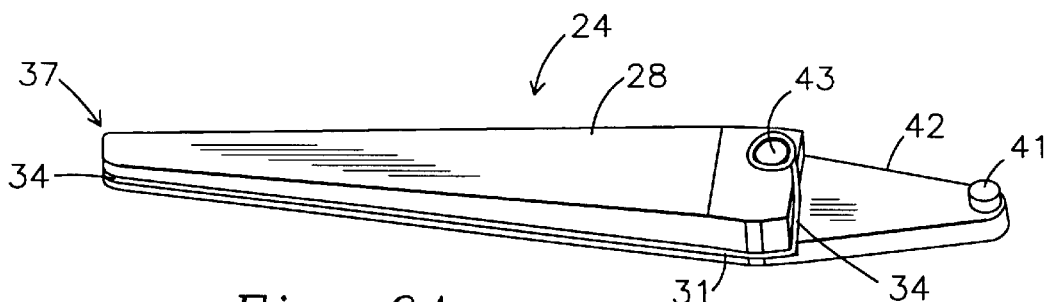
FIG. 6A is a perspective view of a first blade portion on an insulating blank according to the present invention.

Referring to FIG. 6A, an enlarged view of a first end effector, such as scissors blade 24 is provided. In a presently preferred embodiment, a first scissors blade 24 is comprised of a nonconductive blade blank 28 which is preferably constructed of a ceramic material such as Zirconia, Mullite, or Alumina available from Coors Ceramics Company, Inc., but which also might be suitably constructed of rigid plastic or insulated metal.

Figure 6B:
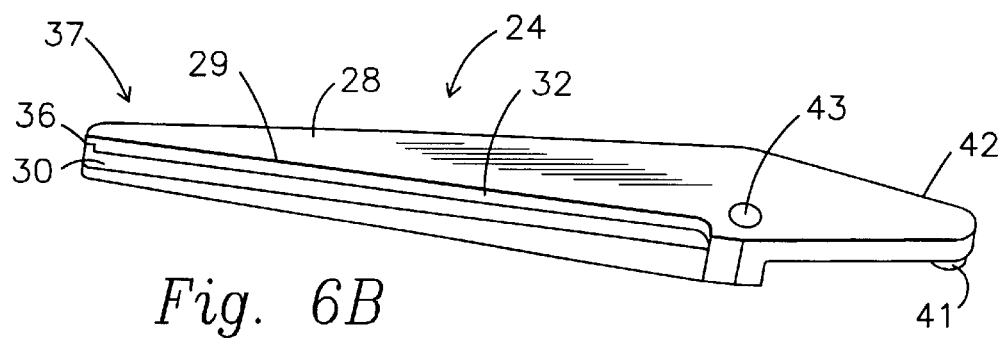
FIG. 6B is a reverse angle view of the first blade portion of FIG. 6A.
Figure 6C:
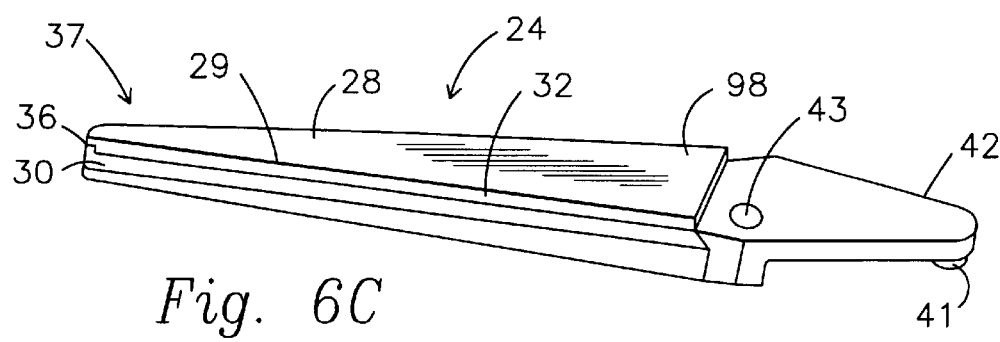
FIG. 6C is an alternatively preferred embodiment of a first blade portion on a conductive blank shown with insulating face portion.

In an alternatively preferred embodiment, illustrated in FIG. 6C, the scissors blade 24 is comprised of a conductive blade blank 28 which is preferably constructed of a traditional metal end effector blank. An insulating section, typically of ceramic material is added to the effector blank to form the face 98 of the interior side of the blade.

At the proximal end 41 of the first blade 24 is a post 41, a function of which will be explained in connection with cam socket 70 shown in FIG. 12. Proceeding from the post 41, or preferably a surface area on the same side of proximal end 42 of first blade 24, perhaps adjacent to aperture 43, is a conductor 34 which proceeds through groove 31 down at least a portion of the end effector, such as blade 24. Preferably, the conductor 34 will proceed to the distal end of the end effector and thereby be connected to the cutting side of the first blade 24 as by connection 36, shown in FIG. 6B. Preferably the conductor 34 is insulated as it proceeds distally showing the end effector to connection 36 to prevent inadvertent RF current discharges into tissue.

The active side of the end effector, such as the cutting side of blade 24 shown in FIG. 6B has an exposed conductive strip 30 offset from the cutting edge 29 by a distance of approximately 0.02 inches (0.58 mm) creating a gap 100 as illustrated in FIGS. 17–19. This offset or recess may vary between about 0.003 inches and 0.2 inches to produce a fulgurating gap with second blade 26 but is preferably between 0.005 inches and 0.050 inches, and is most preferably about 0.015.

Figure 7A:
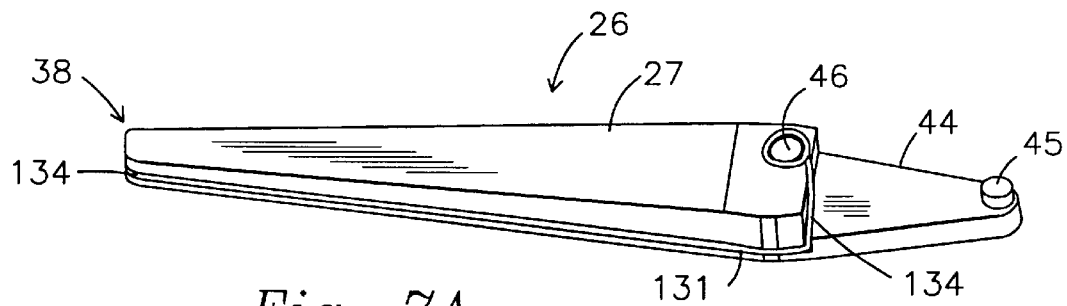
FIG. 7A is a perspective view of a second blade portion according to the present invention.

Referring to FIG. 7A, an enlarged view of a second end effector, such as scissors blade 26 is provided. In a presently preferred embodiment, a second scissors blade 26 is comprised of a nonconductive blade blank 27 which is preferably constructed of a ceramic material such as Zirconia, Mullite, or Alumina available from Coors Ceramics Company, Inc., but which also might be suitably constructed of rigid plastic or insulated metal.

Figure 7B:
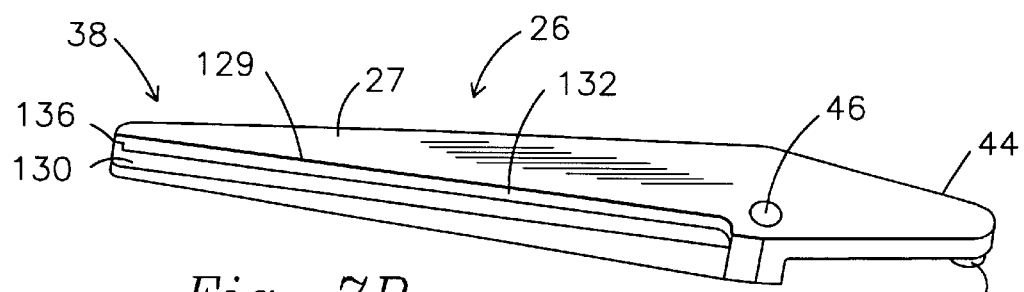
FIG. 7B is a reverse angle view of the second blade portion of FIG. 7A.

FIG. 7B shows the reverse angle of FIG. 7A.

Figure 7C:
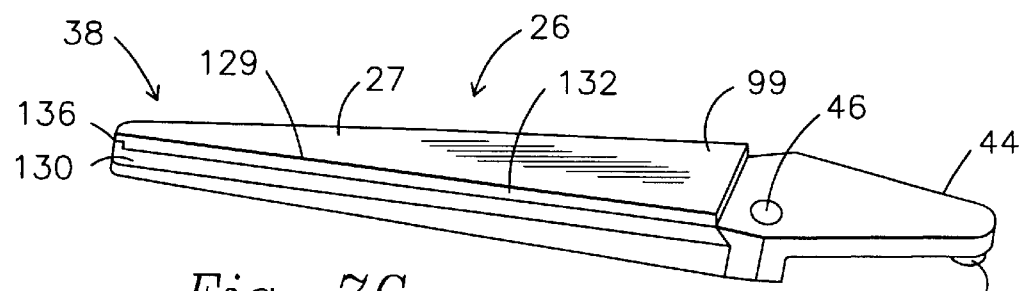
FIG. 7C is an alternatively preferred embodiment of a second blade portion shown with insulating face portion.

FIG. 7C shows an alternatively second blade 26 also having a proximal section 44 with post 45. In this figure, the face 99 protrudes from the interior surface of the blade. Blade 26 also has an aperture 46 which corresponds to aperture 43 on the first blade 24. The second blade may be manufactured from a traditional metal end effector blank 27 or from a non-conductive blade blank 28 depending upon the embodiment chosen by the user. It will be understood that the end effectors may have a variety of shapes and in particular end effectors for scissors may have a curved profile.

The opposing side of the second blade 26 will have an exposed conductive strip 130 which may, or may not, symmetrically correspond to the exposed conductive strip 30 of the first blade. Furthermore, the exposed conductive strip 130 of the second blade 26 may, or may not, be offset from the cutting edge 129 of the second blade. Additionally, the conductive strip 130 may or may not be integral to the second blade 26. The conductive strip 130 would likely be integral to the second blade 26 if a conductive blank were utilized, but it could be affixed separately as well.

Figure 15A:
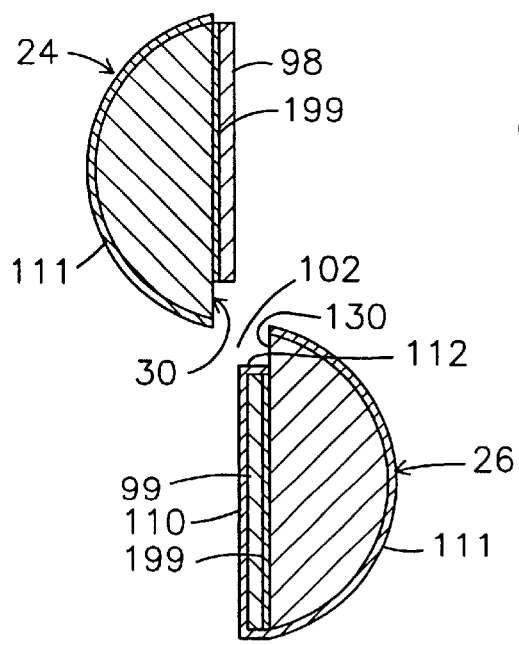
FIG. 15A is a cross-sectional plan view of an alternative embodiment of end effectors.

In a first preferred embodiment illustrated in FIG. 15A, the first and second blades 24, 26 are made of non-conductive blanks and have conductive strips 30, 130 which are both offset from the cutting edges 29, 129 of the cutting sides of the first and second blades 24, 26. Both the first and second blades have gaps 32, 132 created by the offset of their respective conductive strips 30, 130 from their cutting edges 29, 129.

Figure 2:
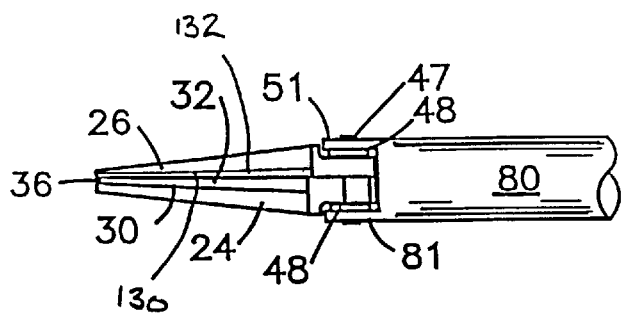
FIG. 2 is a top view of the distal end of a portion of the scissors of FIG. 1.

FIGS. 2–5 and 15A show different views of an embodiment having a second conductive blade 26 and non-conductive embodiment of a first blade 24 mounted in clevis section 80. FIG. 2 is a top view showing connecting rivet 47 holding pressure washers 48, conductive blade 26, and non-conductive blade 24, in alignment between clevis wings 81 so that blades 24 and 26 may move in pivotable relation to each other. It will be understood that a single pressure washer 48 may be sufficient. Shown on first blade 24 is exposed conductive strip 30 offset from cutting edge 29 by gap 32 of approximately 0.02 inches. Shown on second blade 26 is exposed conductive strip 130 offset from cutting edge 129 by gap 132 of approximately 0.02 inches. It will be understood that the fulgurating gap 102 (illustrated in FIG. 15A) may be adjusted for optimal effect between about 0.01 inches and 0.2 inches depending upon the design of a particular set of end effectors. A gap 102 of at least slightly greater than 0.05 inches is generally preferred.

Figure 3:
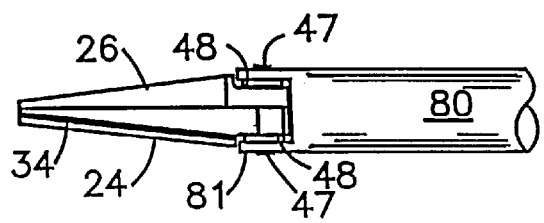
FIG. 3 is a bottom view of the distal end portion of the scissors of FIG. 1.

In the bottom plan view of FIG. 3, the conductor 34 is shown. This conductor 34 connects via connection 36 to the exposed conductive strip 30 (shown in FIG. 2). This design may be utilized in both the first and second blades 24, 26. While it is anticipated that the conductor 34 may be plated or press fit into groove 31 and thereafter covered with an insulating resin, it may also be possible to cast the blade 24 from ceramic or plastic with conductor 34 embedded within the blade blank 28.

Figure 4:
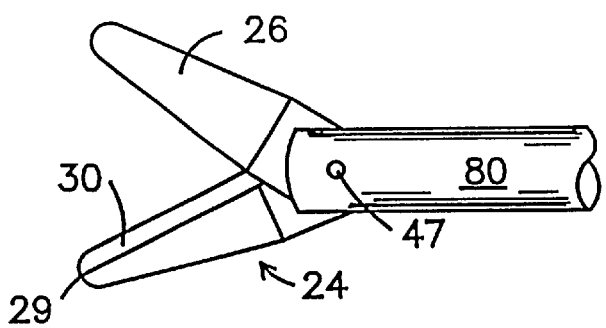
FIG. 4 is a side plan view of the distal end of a portion of the scissors of FIG. 1 in their open position.

FIG. 4 is a left side view showing scissors blades 26 and 24 in their open position. With the cutting side of a non-conductive embodiment of first blade 24 exposed, the conductive strip 30 is shown. If first blade 24 is constructed of a conductive material, there may be no need to have a separate conductor 34 apart from the blade blank 28.

Figure 5:
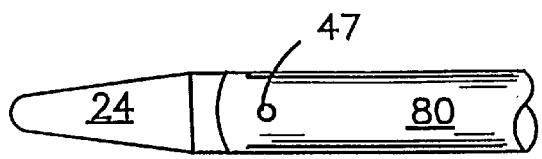
FIG. 5 is a side plan view opposite FIG. 4 of the distal end of a portion of the scissors of FIG. 1 in their closed position.

FIG. 5 shows a right side view with blades 24 and 26 in their closed position so that only first blade 24 is apparent. It will be understood that while the blades 24, 26 shown in these illustrations have a linear profile when observed from the top as in FIG. 2, the blade profiles could alternatively be arcuate if preferred.

Turning now to the assembly of bipolar end effectors, first blade 24 and second blade 26 are mounted in cam socket 70 (shown in FIG. 12). First side 77 and opposed side 78 of cam socket 70 define a channel 74 at the distal end of cam socket 70. At the proximal end of cam socket 70 is aperture 73 which contains first connection strip 75 and second connection strip 76 for the purpose of connecting with electrical connections 52, 54 respectively on push rod 50 shown in FIG. 13. It will be understood that the illustrated connection strips 75, 76 are specifically adapted to conduct current to the posts 45, 41 of the blades 24, 26. It will generally be preferred to conduct current to other surfaces on the blades such as adjacent to apertures 43, 46. It is contemplated that many different mechanisms may be utilized to connect the conductive strips 30, 130 to electrical connections 52, 54 or to any other electrical source as is prescribed by the implement design.

In order to secure the blades with their protruding posts 41, 45, the cam socket 70 may be made of a flexible or elastomeric material such as a plastic polymer such as polyurethane that will permit first side portion 70 and second side portion 78 to be bent apart from each other when blades 24, 26 are inserted. Alternatively, the cam socket 70 may be made of rigid material and the blades 24, 26 inserted in a staggered manner and then aligned at the pivot point represented by apertures 43, 46. The post 41 on first blade 24 is received in groove 71 on the first side 77 of cam socket 70, while post 45 on second 26 is received in groove 72 on the opposed side 78.

Attached to cam socket 70 by means of chemical, dielectric, or other appropriate bonding, is a conductor from connection strip 75 to first cam socket side 77 so that it may interface with the conductor 34 on the first blade 24. Similarly, connective strip 76 is in communication with the second opposed side 78 of cam socket 70 so that an electrical connection can be made with second blade 26. This conductor may be embedded within cam socket 70 or may proceed on the exterior surface of cam socket 70 so as not to connect with connective strip 75 on the interior of first side 77.

When blades 24, 26 are mounted in cam socket 70, push rod 50 (shown in FIG. 13) is inserted into aperture 73 so that connector 52 is in contact with connective strip 75 and connector 54 is in contact with connective strip 76. Although push rod 50 may be a relatively small diameter tube containing insulated wires, it is preferably rigid plastic formed with an internal conductor 51 proceeding from connector 52 internal of push rod 50 to proximal end 53. Also, a second or external conductor on push rod 50 proceeds from connector 54 to the proximal end 53 of push rod 50.

The assembled blade 24, 26, cam socket 70, and push rod 50 assembly is then inserted between opposed wing sections 81 of clevis section 80. The push rod proceeds through lumen 86 of clevis section 80, while the cam socket 70 is received within chamber 85 of the clevis section 80, and ends 37, 38 of blades 24, 26 are protruding. Apertures 43, 46 on blades 24, 26 respectively (shown in FIGS. 6–7), are aligned with apertures 82 on the clevis section 80, optionally with one or more spring washers 48 (shown in FIGS. 2 and 3) and connected by rivet 47 (shown in FIGS. 2 through 5). If desired, this entire assembly of blades, clevis section, cam socket, and push rod may be disposable.

Turning now to FIG. 10, the proximal end of push rod 53 is threaded through lumen 13 beginning at the distal end 16 of tubular barrel 12 until it projects at the proximal end 15. When so positioned, the proximal end 87 of clevis section 80 is fixed in mounting section 17 internal to the tubular barrel. Mounting section 17 and proximal clevis section 87 may be press fitted or preferably will have mating threads for secure positioning. Relatively narrower section 84 of clevis section 80 is received within the proximal end 16 of tubular barrel 12 while relatively wider section 83 of clevis section 80 protrudes from barrel 12.

The next assembly step is for proximal end 15 of tubular barrel 12 to be mounted in aperture 60 of stationary scissors handle 20 (shown in FIG. 9). Protruding fitting segment 23 on stationary handle 20 is in turn received within chamber 19 of tubular barrel assembly 12. The proximal end 53 of push rod 50 protrudes through aperture 60 of stationary handle section 20. Stationary handle 20 has an upper section 64 and a lower handle 63. Also shown is a structure for pivotable attachment with movable handle 21 (shown in FIG. 8) consisting of a clevis like arrangement of two raised circular sections 61 defining between them a gap to receive protruding section 67 on movable handle 21 and each having a threaded aperture 62.

Prior to assembling movable handle section 21 with stationary handle 20, push rod connector 55 is first mounted into the circle and slot configuration 68 of the movable handle 21. Bulbous portion 58 of push rod connector 55 is inserted through the circular section (having a width less than the diameter of bulbous head 58) of opening 68 until the entire bulbous section 58 is internal of movable handle 21 and thereafter push rod connector 55 is slid into the slot section (having a width less than the diameter of bulbous head 58) of opening 68 so that the bulbous head 58 will not pull free. When so positioned, the lumen 56 proceeding through push rod connector 55 is in alignment with an internal two connector plug in communication with external two connector plug 69 at the upper end of movable handle 21.

It should also be noted that aperture 66 of movable handle 21 is sized somewhat larger than aperture 62 on stationary handle 20. The two handle sections 21 and 20 are joined at two points. First, the proximal end 53 of push rod 50 passing through the upper portion 64 of stationary handle section 20 is received through aperture 56 of push rod connector 55 so that it connects through opening 68 into movable handle 21. The proximal end 53 of push rod 50 is thereby placed in electrical connection with tube connector socket 69. The handle sections 20, 21 are also joined by positioning protrusion 67 of moveable handle section 21 in between the clevis like structures 61 on stationary handle 20 and inserting a screw through threaded apertures 62, said screw threads not engaging with the movable scissors handle 21 because of the relatively larger size of aperture 66. This permits free pivoting of the handle sections relative to one another, thereby effecting the pushing or retraction of push end 50 relative to the end effectors.

To utilize bipolar end effectors according to the present invention, plug 69 is connected with appropriate bipolar power source. In use, the positive RF energy proceeds from plug 69 through central electrical connector 51 of push rod 50 to connector 52 at the distal end thereof, and to connective strip 75 of scissors cam socket 70. From connector 70, a current is received by connector 34 on first blade 24. RF current proceeds along conductor 34 toward the distal end of blade 24 until connection 36 allows the current to communicate with the exposed conductive surface 30. Exposed conductive strip 30 is separated by gap 32 from exposed conductive strip 130 of second blade 26. This gap 32 is a space sufficiently narrow to allow RF current to arc through the tissue being held or cut between the first 24 and second 26 end effectors. Because of the gap 32 separating conductive strip 30 from conductive end effector 26, the two end effectors 24 and 26 can touch one another along their entire length as the cutting motion takes place without creating an electrical short circuit between them.

In fact, use of the first and second gaps 32, 132 together has been found to be particularly effective at providing tampon pressure to a particular tissue location. However, one of both first and second gaps 32, 132 is not necessarily required. The first and second gaps 32, 132 have also been found to be effective at housing the conductive strips 30, 130 and ensuring that they do not inadvertently touch. These small electrodes in the notched areas have been found to harness the flow of current in the incision. By harnessing the flow of current in the incision, where it is needed most, the current density is greater. More heat may be generated in this area with less power. Additionally, the current will flow more directly through the incision area. More direct flow of current through the area of the incision will greatly reduce any damage to lateral tissue.

The double gap configuration of using both gaps 32, 132 has been found effective at ensuring that both sides of the incision receive similar amounts of compression as well as RF energy in the form of heat. Furthermore, the double gap configuration has been found to be effective at allowing the incision sight to be heated, or cauterized, as well as compressed, just prior to the cutting cycle. At the location where the incision will occur, the locale has already been treated by RF coagulation and tampon pressure in combination to aide in controlling any bleeding prior to making the cut.

When utilizing the first and second blades 24, 26 to sever a tissue, the gaps 32, 132 on each side of the tissue allows the blades 24, 26 to pinch or compress the incision sight together. This pinching action has been found effective in assisting with tampon pressure and coagulation current. Opposing gaps have been found effective at producing an incision which is hemostatic and denatured with RF cauterization.

The use of the first and second gaps 32, 132 has been found to utilize about half the power of some other bipolar scissor blades (15 watts) and it is possible to show the tissue denatured before a mechanical cut is made.

When it is desired to cauterize tissue, the RF voltage is applied to the electrosurgical scissors thereby making the first blade 26 and exposed conductive strip 30 the active bipolar electrodes. When the scissors are in contact with tissue, the current flows from a portion of the conductive strip at the cutting point or slightly distal thereto through the tissue to a conductive strip on the second blade 26, thereby effecting cauterization at or just slightly in advance of the cutting point between first blade edge 29 and second blade 26. To complete the electrical circuit, RF current proceeds through the second blade 26 to connector 73 on the cam socket 70 which is in contact with connector 54 on push rod 50, which is in turn connected to the negative polarity at connector 69. This can be accomplished by using a similar system as utilized in the first blade or a different system. Obviously, the use of a conductive second blade 26 with an exposed conductive strip 130 would be able to conduct electricity to the connector 74 in contact with push rod connector 54. The design of end effectors in accordance with the invention permits the current to cross before the blades pass one another thereby creating fulguration in advance of the cut and reducing the energy setting required to ensure that the sharply dissected tissue will be provided its sufficient RF energy to cauterize.

In heat generating dissection devices the charring of tissue is a common and undesirable side effect. The buildup of charred tissue on electrosurgical devices is common and is typically addressed either by cooling the cutting surfaces of the end effector, as with water, or by using a nonstick surface. Reduced energy settings, as permitted by the present invention, is a solution to the charring and buildup problems. If the RF energy needed to control bleeding is low, the tissue is denatured, and cooked like the white of an egg without burning where the tissue is blanched rather than charred. Tissues are thus sealed and sticking is minimized.

The present invention promotes the efficient use of RF energy by containing the flow of positively charged energy particles through a well defined positive electrode 30 just prior to the tissue cutting point. Some of the current is absorbed to heat the tissue and the remaining positive energy is pulled into the negative electrode 130, thus minimizing the escape of energy from the instrument into surrounding tissues. The novel design focuses the RF energy to reduce the amount of energy required to produce coagulation at the cutting site and to effectively remove the residual energy from the patient's body without affecting other tissues. Lower energy settings result in less char and buildup in the instrument in addition to reducing the likelihood that the energy will affect other tissue or organs.

The first and second blades 24, 26 need not be constructed of the same material according to the present invention. Looking to FIG. 15, the first and second blades 24, 26 may both be constructed of a non-conducting material. Alternatively, one may be constructed of a conducting material while the other constructed of a non-conducting material. Finally, both blades may be constructed out of conductive materials.

Figure 15B:
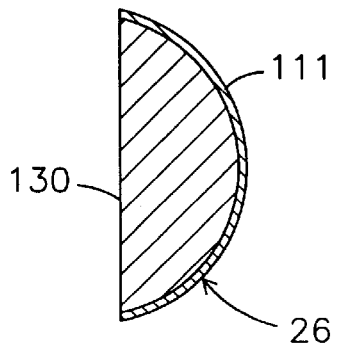
FIG. 15B is a variant of the embodiment of FIG. 15A where the second blank is conductive.

Exterior to at least one, and preferably both, of the blades 24, 26 is insulating surface 111. The portions with cutting edges 29,129 are illustrated as faces 98, 99 which utilize adhesive 198,199 for mounting on a blade. The insulating surfaces 110, 111, 112 are illustrated substantially encapsulating the first and second blades 24, 26, with the exception of the conductive strips 30, 130. The insulating surfaces 110, 111, 112 have been found to be effective in directing the flow of RF energy to reduce, if not eliminate RF energy flow through the back of the blade as well as other portions of the blade. The insulating surfaces 110, 111, 112 assist in forcing the current to travel through the first conductor strip 30 through tissue and into the other conductive strip 130. This insures that current density is maximized and focused in the incision which is more efficient and allows less stray current to damage lateral tissue and provides improved RF coagulation at lower power settings. It will be appreciated, as shown in FIG. 15B with a metal blade 26 that the entire interior surface of the blade can serve as the conductive area 130, provided that the first blade 24 focuses its conductive areas along a defined strip 30.

In a preferred embodiment, insulating surfaces 111, 110, 112 surround the outer surfaces of the blades except for the conductive strips 30, 130. However this amost encapsulating design is not required. Additionally, insulating surfaces 111, 110, 112 are located on the faces of each blade to assist in focusing RF energy to travel almost exclusively between the conductive strips 30, 130 and tissue being compressed in the gap between the strips. Insulating material may be any material or substance known in the art to provide a relatively high resistance to electrical current flow relative to the resistance offered by the conductive strips 30,130. Polyimide, polyamide and ceramics are preferred materials.

Insulating surfaces 111 on the outer surfaces of blades 24, 26 are believed to prevent, or limit, the inadvertent transmission of RF energy to unwanted locations which may come into contact with outer surfaces of the blades. Insulating surface portions 111 may only cover a portion of the outer surface of a blade, or may cover the entire outer surface of the blade.

It is also only necessary for only one of the blades to have facing insulating portions 110. Insulating portion 112 on the cutting edge may also be helpful. Although interior insulating surfaces 110, 112 may be located on a single blade, this improvement has been found to be effective at directing the RF energy through the conductive strips 30, 130 when utilized on both blades as well. Although a non-conductive blade may be insulated, or be inherently insulated, it is also possible for a conductive blade to be insulated with any of insulating surfaces 110, 111, 112. In one preferred embodiment, insulating surface 111 is utilized without insulating surfaces 112 and 110 as illustrated in FIG. 15B. Utilizing a non-conductive blade, which is inherently insulated, and an uninsulated conductive blade has been found to allow for efficient manufacturing as only one blade, the non-conductive blank, will need multiple manufacturing operations.

In another embodiment, a metal face 98,99 is utilized on the first and second blades as shown in FIG. 15A. However, the metal cutting blade portions need not extend the complete length of the blades 24, 26. These metal cutting surfaces may be placed atop either conductive or non-conductive blade blanks having conductive strips 130, 30 utilizing adhesives.

The adhesive may act to assist in insulating the metal electrodes from the metal faces. Although adhesive is used in this alternatively preferred embodiment, any insulating material may be found to function properly. The portion of the metal face proximate to the blade is insulated so that current will flow through the conductive strip in the blade and not primarily through the metal face. It is also contemplated that only one of the blades utilizes a metal face. For instance, a preferred constrocution of the blades of FIG. 15A, face 98 is an insulated ceramic material and face 99 is metal. Other embodiments include metal blades which may or may not have a separate metal face and ceramic blades which may utilize a ceramic face or a separate metal face.

Figure 16A:
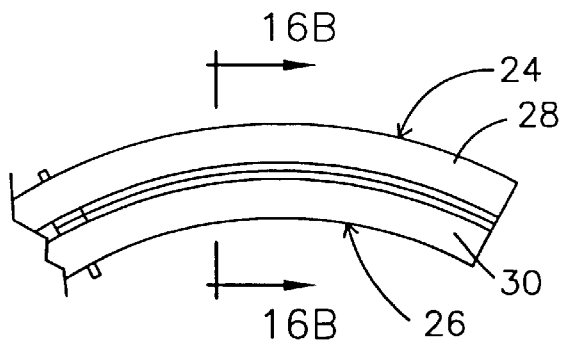
FIG. 16A is a top view of yet another alternative embodiment of end effectors.
Figure 16B:
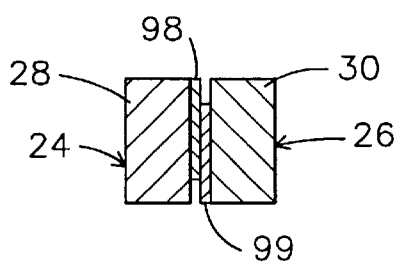
FIG. 16B is a cross sectional view of the end effectors of FIG. 16A taken along line B—B.
Figure 16C:
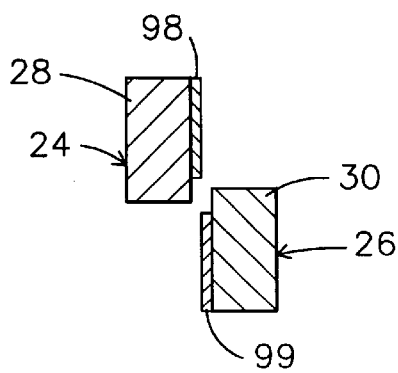
FIG. 16C is a cross section view with the end effectors open.

FIGS. 16A, 16B, and 16C are illustrations of an alternatively preferred embodiment having curved first and second blades 24,26. For some applications, curved blades 24,26 may be preferred. The curved blades 24,26 are illustrated as being constructed of first and second blanks 28,30 with the interior portions having faces 98,99 attached thereto. In one application, the first face 98 has been a ceramic material connected to a conductive first blank 28. The second blank 30 in this embodiment is also conductive, and has a metal face 99 connected thereto. Other blade materials and constructions as taught herein could also be utilized with the curved blade embodiment.

Additionally, cauterization occurring slightly forward of the cutting action of the scissors tends to be more effective and minimizes bleeding from the tissue and other described difficulties in utilizing bipolar instruments during surgery.

Alternative electrical connections may be possible that still permit the rotation of barrel 12 upon turning knob 18 without causing a loss of current to the end effectors. As shown in FIGS. 6, 7, and 12, the novel cam socket 70 of the present invention obviates the necessity for placing a slot in first blade blank 28 to effect the scissors action. Instead, the first blank 28 is only weakened by a single aperture 43. If multiple holes or substantial slots were cut in first blank 28, it would substantially increase the risk of mechanical failure of the first blank. Accordingly, the present blade post and cam socket design is a substantial improvement over prior art blade design such as those depicted in FIG. 8 of U.S. Pat. No. 5,391,166.

The electrode surface 30 of the first blade 24 is designed not to contact the second blade 26 and is separated by the fulgurating gap 32 to coagulate tissue. The interference friction between the cutting edge 129 and face 98 of first blade 24 does not harm the electrode surface 30 of the non-conductive blade 24 as there is no physical contact or wearing of that conductive surface 30 along the cutting edge 29.

Exposure of the positive RF flow from the electrode surface 30 of first blade 24 to tissue and return through the second blade 26, as shown in FIGS. 6A, 6B, 7a and 7B is a unique design to ensure energy flow from the distal end of the end effector toward the proximal end. To ensure this effect, the exposed conductive strip 30 may be selected from an imperfect conductor such as stainless steel or conductive plastics or ceramics in lieu of usual gold plate designs.

The specific embodiments described are provided just by way of explanation rather than limitation. All variations that do not depart from the spirit of the invention are intended to be covered by the appended claims.

We claim:

1. A bipolar surgical instrument comprising first and second interfacing end effectors wherein at least one of said first and second end effectors is pivotable relative to the other, and wherein said second end effector has an interfacing side and an electrically conductive interior surface portion and said first end effector has a proximal end, a distal effector end, an interfacing side, and an opposed side, and comprises:

a first blank having a cutting edge on its interfacing side; and a conductor beginning toward the proximal end of said first blank and proceeding toward the distal effector end and connecting to an exposed electrode on the interfacing side of said first blank; and said exposed electrode is electrically isolated and recessed from the cutting edge by a distance of at least about 0.005 inches.

2. The bipolar instrument of claim 1 wherein the exposed electrode is recessed from the cutting edge by approximately 0.020 inches.

3. The bipolar instrument of claim 1 wherein said second end effector has a proximal end, a distal effector end, an interfacing side and an opposed side and wherein a post protrudes from the opposed side of the proximal end of each of said first and second end effectors.

4. The bipolar instrument of claim 1 wherein the recessed exposed electrode of the first end effector creates a fulgurating gap with the electrically conductive portion of the second end effector when the instrument is connected to an RF power supply.

5. The bipolar instrument of claim 4 wherein the opposed side of the first end effector has an electrically non-conductive surface.

6. The bipolar instrument of claim 1 wherein said second end effector has a proximal end and a distal effector end and further comprises:

a second blank having a cutting edge on its interfacing side and a conductor beginning toward the proximal end of said second blank and proceeding toward the distal effector end and connecting to an exposed electrode on the interfacing side; and said exposed electrode is recessed from the cutting edge by a distance of at least about 0.005 inches.

7. The bipolar instrument of claim 1 wherein at least one of the first or second end effectors further comprises a metal face portion on the interfacing side.

8. The bipolar instrument of claim 7 wherein the metal face portion is adhered to said at least one of the first or second end effectors.

9. A method of surgically dissecting and cauterizing tissue comprising the steps of:

(a) connecting a regulated RF power supply to a bipolar surgical scissors having a handle with an actuator in communication with first and second interfacing end effectors wherein:

at least one of said first and second end effectors is pivotable relative to the other in response to the actuator;

said second end effector has an interfacing side with an electrically conductive portion and is electrically connected to the RF power supply;

said first end effector has a proximal end, a distal effector end, an opposed side, an interfacing side with a working surface, and an electrically conductive portion electrically connected to the RF power supply which proceeds toward the distal effector end and is connected to an exposed electrode on the interfacing side, said exposed electrode being recessed from the working surface; and at least when actuated, the working surface of the first end effector contacts the second end effector and the exposed electrode recessed from the working surface is sufficiently proximate to the electrically conductive portion of the second end effector to create a fulgurating gap there between;

(b) placing tissue between said first and second end effectors;

(c) energizing the desired RF power output to the bipolar surgical scissors;

(d) utilizing the actuator to cause the first and second end effectors to pivot relative to one another such that the working surface of the first end effector dissects the tissue as it contacts the second end effector;

(e) thereby placing the exposed electrode in sufficient proximity to the tissue and conductive portion of the second end effector that RF energy from the power supply proceeds distally along the electrically conductive portion on the first end effector to the exposed electrode and thereafter flilgurating into the tissue distal of the dissection, and to the electrically conductive portion of the second end effector, thereby at least partially desiccating and cauterizing the tissue.

10. The method of claim 9 wherein there is no physical contact between the exposed electrode of the first end effector and the electrically conductive portion of the second end effector.

11. A bipolar surgical instrument comprising:

(a) a first end effector having an interfacing side with a face and an opposed side;

(b) a second end effector pivotable relative to said first end effector and having an interfacing side and an opposed side;

(c) an electrode located on the interfacing side of the first end effector, said electrode being recessed from the face of said interfacing side; and (d) a conductive portion on the interfacing side of said second end effector.

12. The bipolar instrument of claim 11 wherein when the first and second end effectors are interfacing, the electrode of the first end effector is separated from the interfacing side of said second end effector by a gap of approximately 0.020 inches.

13. The bipolar surgical instrument of claim 11 wherein the interfacing side of said second end effector has a metal face.

14. The bipolar surgical instrument of claim 13 wherein said metal face is adhered to said second end effector.

15. The bipolar surgical instrument of claim 11 wherein said opposed sides of said first and second end effectors are insulated.

16. The bipolar surgical instrument of claim 11 wherein the conductive portion of the second end effector is a recessed electrode.

17. The bipolar surgical instrument of claim 13 wherein the metal face is covered with an insulating material.

18. The bipolar surgical instrument of claim 11 wherein the first end effector comprises a conductive blank with a non-conductive face adhered thereto.

19. The bipolar surgical instrument of claim 18 wherein the non-conductive face is a ceramic material.

20. The bipolar surgical instrument of claim 18 wherein the non-conductive face is metal covered by an insulating material.

* * * * *